United States Patent [19]
Hashimoto et al.

[11] Patent Number: 5,866,632
[45] Date of Patent: Feb. 2, 1999

[54] DENTAL OR SURGICAL ADHESIVE AND POLYMERIZATION INITIATOR COMPOSITION FOR THE SAME

[75] Inventors: Isao Hashimoto; Masami Arata; Weiping Zeng, all of Moriyama, Japan

[73] Assignee: Sun Medical Co., Ltd., Moriyama, Japan

[21] Appl. No.: 695,771

[22] Filed: Aug. 8, 1996

[30] Foreign Application Priority Data

Aug. 10, 1995 [JP] Japan ................................. 7-204748

[51] Int. Cl.$^6$ ............................... C08F 4/52; C08K 5/07
[52] U.S. Cl. ...................... 523/118; 524/183; 524/533; 526/195; 526/196; 433/228.1
[58] Field of Search ..................... 433/228.1; 526/195, 526/196; 523/118; 524/183, 533

[56] References Cited

U.S. PATENT DOCUMENTS

| | | | |
|---|---|---|---|
| 4,515,724 | 5/1985 | Ritter | 554/77 |
| 4,639,498 | 1/1987 | Ritter | 526/196 |
| 4,676,858 | 6/1987 | Ritter | 526/195 |
| 4,918,136 | 4/1990 | Kawaguchi et al. | 523/118 |
| 5,252,629 | 10/1993 | Imai et al. | 523/118 |
| 5,264,513 | 11/1993 | Ikemura et al. | 523/116 |
| 5,530,038 | 6/1996 | Yamamoto et al. | 523/118 |

FOREIGN PATENT DOCUMENTS

| | | |
|---|---|---|
| 0051797 | 10/1981 | European Pat. Off. . |
| 0567213 | 10/1993 | European Pat. Off. . |
| 4811892 | 2/1973 | Japan . |
| 5137092 | 10/1976 | Japan . |
| 354683 | 8/1991 | Japan . |
| 3264509 | 11/1991 | Japan . |
| 370753 | 11/1991 | Japan . |
| 5253284 | 10/1993 | Japan . |
| 68301 | 2/1994 | Japan . |

Primary Examiner—Andrew E. C. Merriam
Attorney, Agent, or Firm—Sherman and Shalloway

[57] ABSTRACT

A polymerization initiator composition comprising 100 parts by weight of an organic boron compound (A) and 10 to 150 parts by weight of an aprotic solvent (B) having a boiling point of 30° to 150° C.; and a dental or surgical adhesive composition containing the above polymerization initiator composition.

6 Claims, No Drawings

DENTAL OR SURGICAL ADHESIVE AND POLYMERIZATION INITIATOR COMPOSITION FOR THE SAME

DETAILED DESCRIPTION OF THE INVENTION

This invention relates to a dental or surgical adhesive composition and a polymerization initiator composition for the same. More specifically, it relates to a dental or surgical adhesive composition having high bond performance and a polymerization initiator composition used for the same and having improved safety against ignition when it sticks to paper or the like.

JP-B 37092/1976 (the term "JP-B" as used herein means an "Japanese patent publication") discloses a dental or surgical adhesive which comprises a product (partially oxidized trialkyl boron) obtained by reacting a trialkyl boron with 0.3 to 0.9 mole of oxygen as a polymerization initiator.

The trialkyl boron, as disclosed in the publication, is extremely unstable in air and extremely dangerous for handling because it reacts with oxygen drastically and ignites when it is exposed to air. JP-B 37092/1976 proposes a polymerization initiator which has improved safety against ignition by suppressing a reduction in the activity of the trialkyl boron as much as possible. However, it is not satisfactory.

JP-A 11892/1973 (the term "JP-A" as used herein means an "unexamined published Japanese patent application") discloses a process in which a hydrophobic and viscous substance such as vaseline, paraffin, silicone (silicon oil) or the like and an absorber such as silicic acid or alumina as required are added to a trialkyl boron or a derivative thereof to prepare a paste to improve safety against ignition.

JP-B 54683/1991 (corresponding to U.S. Pat. No. 4,676,858 and EP Patent 78994) proposes a polymerization initiator which is a uniform mixture obtained by adding an organic oligomer or organic polymer such as silicon oil, wax, oligoester or oligoamide to an organic boron compound.

JP-A 264509/1991 proposes a process in which a polymer of alkyl (meth)acrylate is added to tributyl boron or partially oxidized tributyl boron to prepare a paste to improve safety against ignition.

Further, a proposal for providing the butyl group of tributyl boron with a structure which hardly ignites in air is disclosed in EP-51797, JP-A 70753/1991, West German Patent 3201731, JP-A 253284/1993 and JP-B 8301/1994.

It is therefore an object of the present invention to provide a polymerization initiator composition which does not cause scorching or ignition when it is contacted with paper or the like in air, is a low-viscosity liquid or paste having high fluidity, and is activated by oxygen contained in air to provide a polymerizable composition with high polymerization activity to cure in a short period of time.

Another object of the present invention is to provide a polymerization initiator composition having high fluidity and especially being suitable for use in a dental adhesive composition, which can be obtained accurately in such a small amount that the amount of the composition used at one time is as small as several milligrams or several tens of milligrams.

A further object of the present invention is to provide a dental or surgical adhesive composition which comprises the above polymerization initiator composition of the present invention and shows high bond performance.

Other objects and advantages of the present invention will become apparent from the following description.

According to the present invention, the above objects and advantages of the present invention are, firstly, attained by a polymerization initiator composition which comprises (A) 100 parts by weight of an organic boron compound and (B) 10 to 150 parts by weight of an aprotic solvent having a boiling point of 30° to 150° C..

Preferred examples of the organic boron compound (A) used in the present invention include a trialkyl boron, alkoxy alkyl boron, dialkyl borane and partially oxidized trialkyl boron. They may be used alone or in combination of two or more.

Examples of the trialkyl boron include triethyl boron, tripropyl boron, triisopropyl boron, tributyl boron, trisec-butyl boron, triisobutyl boron, tripentyl boron, trihexyl boron, trioctyl boron, tridecyl boron, tridodecyl boron, tricyclopentyl boron, tricyclohexyl boron and the like.

Examples of the alkoxyalkyl boron include butoxydibutyl boron and the like.

Examples of the dialkyl borane include butyldicyclohexyl borane, diisoamyl borane, 9-boricyclo[3.3.1]nonane and the like.

Examples of the partially oxidized trialkyl boron include partially oxidized tributyl boron and the like. The partially oxidized trialkyl boron is obtained by adding preferably 0.3 to 0.9 mole, more preferably 0.4 to 0.6 mole, of oxygen to one mole of the trialkyl boron.

Among these organic boron compounds, tributyl boron or partially oxidized tributyl boron gives especially good results. The most preferred organic boron compound is partially oxidized tributyl boron.

As the aprotic solvent (B), a solvent having a boiling point of 30° to 150° C. is used. The boiling point is preferably in the range of 30° to 120° C., more preferably in the range of 30° to 80° C..

The aprotic solvent (B) preferably is the one which does not reduce the bond performance of the adhesive composition and does not remain in the cured composition by volatilization and scattering.

Preferred examples of the aprotic solvent (B) include solvents having no active hydrogen which reacts with the organic boron compound (A) and is present in a hydroxy group or mercapto group and being capable of forming an uniform solution with the organic boron compound (A).

Illustrative examples of the aprotic solvent (B) include hydrocarbons such as pentane, hexane, cyclohexane, heptane, benzene and toluene; halogenated hydrocarbons such as chlorobenzene, fluorobenzene, dichloroethane and freon; ethers such as diethyl ether, diisopropyl ether, ethyleneglycol dimethylether and tetrahydrofuran; ketones such as acetone, methyl ethyl ketone and diethyl ketone; and esters such as methyl acetate, ethyl acetate and isopropyl acetate Of these, ketones, ethers and esters are preferred, and acetone, methylethyl ketone and ethyl acetate are particularly preferred.

These aprotic solvents (B) may be used alone or in combination of two or more.

The polymerization initiator composition comprising the above components (A) and (B) of the present invention (1) does not cause scorching or ignition when it is contacted with paper or the like in air, (2) is a low-viscosity liquid having high fluidity, and (3) exhibits high polymerization activity when it is activated by hydrogen contained in air.

It is possible to further increase the safety level against ignition of the polymerization initiator composition of the present invention by further containing a liquid or solid organic oligomer or organic polymer (C), which is inert to the organic boron compound.

Preferred examples of the organic oligomer or polymer include liquid paraffin, liquid or solid low molecular weight polyethylene, solid vaseline, solid wax, liquid or solid alkyl (meth)acrylate (co)polymers, and the like.

Illustrative examples of (co)polymers of the alkyl (meth) acrylate include polymers of alkyl acrylate such as methyl acrylate, ethyl acrylate, propyl acrylate, isopropyl acrylate, butyl acrylate, sec-butyl acrylate, isobutyl acrylate, t-butyl acrylate, pentylacrylate and hexyl acrylate; polymers of alkyl (meth)acrylate such as methyl methacrylate, ethyl methacrylate, propyl methacrylate, isopropyl methacrylate, butyl methacrylate, sec-butyl methacrylate, isobutyl methacrylate, t-butyl methacrylate, pentyl methacrylate and hexyl methacrylate and copolymers thereof; and copolymers of these monomers and styrene and butadiene.

Of these, homopolymers of propyl methacrylate, butyl methacrylate, isobutyl methacrylate and pentyl methacrylate and copolymers of these monomers and methyl methacrylate are preferred, and a copolymer of butyl methacrylate or isobutyl methacrylate and methyl methacrylate are particularly preferred.

The content of the methyl methacrylate in the copolymer is preferably 50 mole % or less, more preferably 30 mole % or less, in view of solubility or dispersibility of the copolymer into an organic boron compound.

As the organic oligomer or polymer, a homo- or co-oligomer or home- or copolymer of alkyl (meth)acrylate is preferred.

Further, the solid organic oligomer or polymer is more preferable than the liquid organic oligomer or polymer.

In the polymerization initiator composition of the present invention, particularly preferably, the organic boron compound is partially oxidized tributyl boron, the aprotic solvent is acetone, and the polymerization initiator composition further contains a liquid or solid organic oligomer or polymer which is inert to the organic boron compound, and the organic oligomer or polymer is a co-oligomer or copolymer of methyl methacrylate and (iso)butyl methacrylate.

The polymerization initiator composition of the present invention contains 10 to 150 parts by weight of an aprotic solvent (B) and, if necessary, 5 to 100 parts by weight of an organic oligomer or polymer (C) based on 100 parts by weight of the organic boron compound (A). The polymerization initiator composition of the present invention preferably comprises 20 to 100 parts by weight of an aprotic solvent (B) and, if necessary, 5 to 100 parts by weight of an organic oligomer or polymer (C), more preferably 30 to 80 parts by weight of an aprotic solvent (B) and, if necessary, 10 to 80 parts by weight of an organic oligomer or polymer (C) based on 100 parts by weight of the organic boron compound (A).

According to the present invention, there is provided a dental or surgical adhesive composition which comprises the above polymerization initiator composition of the present invention.

That is, according to the present invention, there is provided a dental or surgical adhesive composition which comprises 30 to 90 parts by weight of a polymerizable monomer (a), 0 to 60 parts by weight of a (meth)acrylate polymer (b) and 1 to 30 parts by weight of the above polymerization initiator composition (c) of the present invention based on 100 parts by weight of the total of the components (a), (b) and (c).

In the adhesive composition of the present invention, a known monofunctional monomer or polyfunctional monomer can be used as the polymerizable monomer (a) without restriction. (Meth)acrylate monomers are preferably used because they are not so stimulative to the human body. Polymerizable monomers having an acidic group in the molecule are preferred as a component for providing high adhesive strength to dentin. Therefore, a combination of (meth)acrylate and a polymerizable monomer having an acidic group is also preferably used.

Illustrative examples of the monofunctional (meth) acrylate include alkyl (meth)acrylates such as methyl (meth) acrylate, ethyl (meth)acrylate, propyl (meth)acrylate, butyl (meth)acrylate, hexyl (meth)acrylate, 2-ethylhexyl (meth) acrylate, dodecyl (meth)acrylate, lauryl (meth)acrylate, cyclohexyl (meth)acrylate, benzyl (meth)acrylate and isobornyl (meth)acrylate; hydroxyalkyl (meth)acrylates such as 2-hydroxyethyl (meth)acrylate, 2- or 3-hydroxyproypl (meth)acrylate, 4-hydroxybutyl (meth) acrylate, 5-hydroxypentyl (meth)acrylate, 6-hydroxyhexyl (meth)acrylate, 1,2- or 1,3-dihydroxypropyl mono(meth) acrylate and erythritol mono(meth)acrylate; polyethylene glycol mono(meth)acrylates such as diethylene glycol mono (meth)acrylate, triethylene glycol mono(meth)acrylate, polyethylene glycol mono(meth)acrylate and polypropylene glycol mono(meth)acrylate; (poly)glycol monoalkyl ether (meth)acrylates such as ethylene glycol monomethyl ether (meth)acrylate, ethylene glycol monoethyl ether (meth) acrylate, diethylene glycol monomethyl ether (meth) acrylate, triethylene glycol monomethyl ether (meth) acrylate, polyethylene glycol monomethyl ether (meth) acrylate and polypropylene glycol monoalkyl ether (meth) acrylate; fluoroalkyl (meth)acrylates such as perfluorooctyl (meth)acrylate and hexafluorobutyl (meth)acrylate; silane compounds having a (meth)acryloxyalkyl group such as γ-(meth)acryloxypropyltrimethoxysilane(trimethoxy)siiane; and γ-(meth)acryloxypropyltrimethoxysilane(trimethyloxy) silane; (meth)acrylates having a hetero ring such as tetrafurfuryl (meth)acrylate; and the like.

Illustrative examples of the polyfunctional (meth)acrylate include poly(meth)acrylates of alkane polyol such as ethylene glycol di(meth)acrylate, propylene glycol di(meth) acrylate, butylene glycol di(meth)acrylate, neopentyl glycol di(meth)acrylate, hexylene glycol di(meth)acrylate, trimethylo-propane tri(meth)acrylate and pentaerythritol tetra(meth)acrylate; polyoxyalkane polyol poly(meth) acrylates such as diethylene glycol di(meth)acrylate, triethylene glycol di(meth)acrylate, polyethylene glycol di(meth) acrylate, dipropylene glycol di(meth)acrylate, polypropylene glycol di(meth)acrylate, dibutylene glycol di(meth)acrylate and dipentaerythritol hexa(meth)acrylate; aliphatic and aromatic di(meth)acrylates represented by the following formula (1):

$$\begin{matrix} CH_2 & & & & CH_2 \\ \| & & & & \| \\ C-C-O-(CH_2CH_2O)_m-R^1-(OCH_2CH_2)_n-O-C-C \\ | \;\; \| & & & & \| \;\; | \\ R \;\; O & & & & O \;\; R \end{matrix} \quad (I)$$

wherein R is a hydrogen atom or a methyl group, m and n are the same or different and a number of 0 to 10, and $R^1$ is represented by the following formulae:

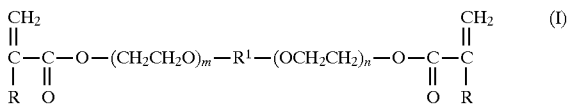

-continued

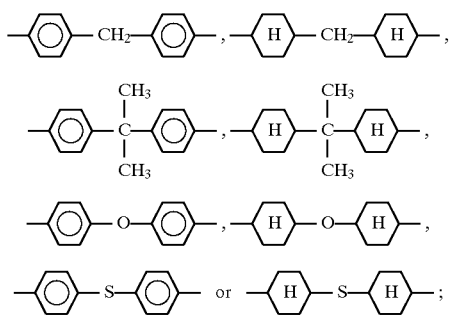

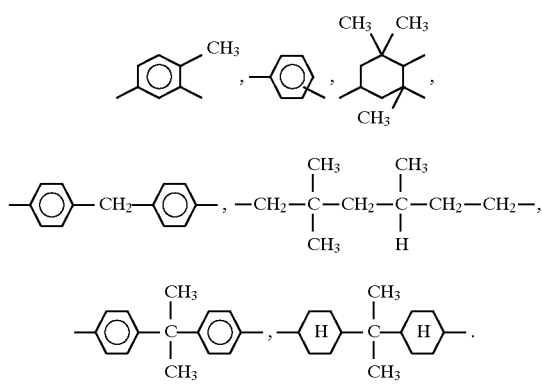

aliphatic and aromatic epoxy di(meth)acrylates represented by the following formula (2):

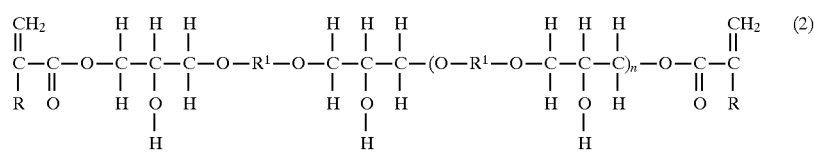

wherein R is a hydrogen atom or a methyl group, n is a number of 0 to 10 and $R^1$ is represented by the following formulae:

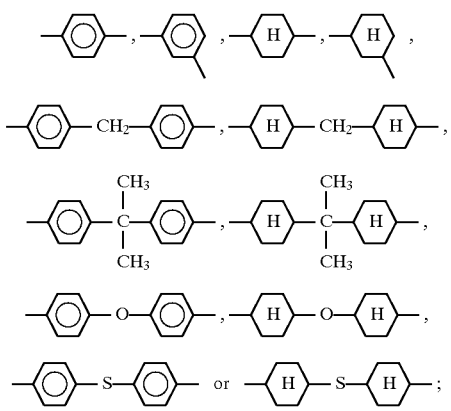

polyfunctional (meth)acrylates having an urethane linkage in the molecule and represented by the following formula (3):

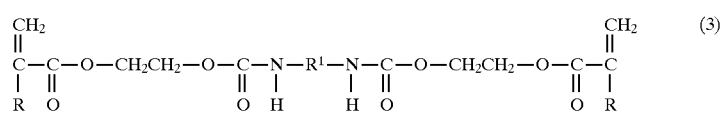

wherein R is a hydrogen atom or a methyl group and $R^1$ is represented by the following formulae:

Of these, particularly preferred monofunctional (meth)acrylates are alkyl (meth)acrylates such as methyl (meth)acrylate and ethyl (meth)acrylate; (meth)acrylates having a hydroxyl group such as 2-hydroxyethyl (meth)acrylate, 1,3-dihydroxypropyl mono(meth)acrylate and erythritol mono(meth)acrylate; (meth)acrylates having an ethylene glycol chain in the molecule such as triethylene glycol monomethyl ether (meth)acrylate and triethylene glycol mono(meth)acrylate; and the like.

Particularly preferred polyfunctional (meth)acrylates are di(meth)acrylates having an ethylene glycol chain in the molecule such as triethylene glycol di(meth)acrylate and polyethbylene glycol di(meth)acrylate, compounds represented by the following formula (1)-a:

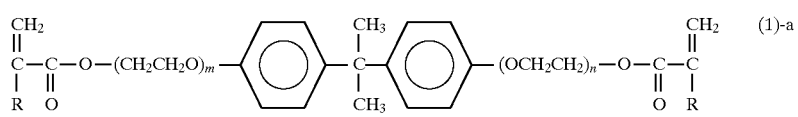

wherein R, m and n are defined the same as in the above formula (1), a compound represented by the following formula (2)-a:

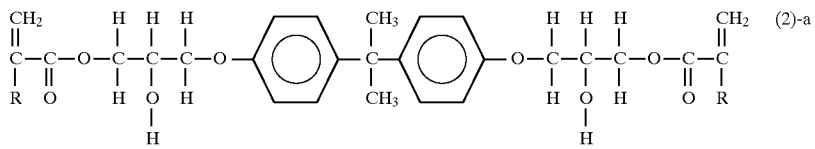

wherein R is defined the same as in the above formula (2), and a compound represented by the following formula (3)-a:

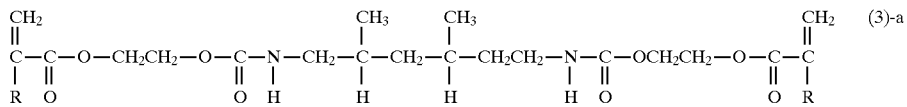

wherein R is defined the same as in the above formula (3).

They may be used alone or in combination of two or more.

Illustrative examples of the polymerizable monomer having an acidic group in the molecule include monomers having a carboxylic acid group or an anhydride thereof such as (meth)acrylic acid and an anhydride thereof, 1,4-di(meth)acryloxyethyl piromellitic acid, 6-(meth)acryloxyethyl naphthalene 1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth)acryloxyethyl trimellitic acid and an anhydride thereof, 4-(meth)acryloxybutyltrimellitic acid and an anhydride thereof, 4-(meth)acryloxydecyltrimellitic acid and an anhydride thereof, 2-(meth)acryloyloxybenzoic acid, 3-(meth)acryloyloxybenzoic acid, 4-(meth)acryloyloxybenzoic acid, β-(meth)acryloyloxyethyl hydrogen succinate, β-(meth)acryloyloxyethyl hydrogen maleate, β-(meth)acryloyloxyethyl hydrogen phthalate, 11-(meth)acryloyloxy-1,1-undecanedicarboxylic acid and pvinylbenzoic acid; monomers having a phosphoric acid group such as (2-(meth)acryloxyethyl)phosphoric acid, (2(meth)acryloxyethylphenyl)phosphoric aid and 10-(meth)acryloxydecylphosphoric acid; and monomers having a sulfonic acid group such as p-styrene sulfonic acid and 2-acrylamide-2-methylpropane sulfonic acids These acidic monomers may be used alone or in combination The amount of a polymerizable monomer having an acidic group is preferably 2 to 20 parts by weight based on 100 parts by weight of all the polymerizable monomers (a).

Illustrative examples of the (meth)acrylate polymer (b) contained in the adhesive composition of the present invention include non-crosslinkable polymers such as polymethyl (meth)acrylate, polyethyl (meth)acrylate, methyl (meth)acrylate ethyl (meth)acrylate copolymer, methyl (meth)acrylate-butyl (meth)acrylate copolymer and methyl (meth)acrylate-styrene copolymer; and crosslinkable polymers such as methyl (meth)acrylate.ethylene glycol di(meth)acrylate copolymer, methyl (meth)acrylate·triethylene glycol di(meth)acrylate copolymer and copolymer of methyl (meth)acrylate and a butadiene-based monomer. Inorganic particles prepared by coating a metal oxide or metal salt with these alkyl methacrylate polymers can be used as the component (b). The component (b) which has been mixed with the component (a) beforehand may also be used.

The adhesive composition of the present invention preferably contains the component (a) in an amount of 30 to 90 parts by weight, the component (b) in an amount of 0 to 55 parts by weight and the component (c) in an amount of 3 to 25 parts by weight. In this case, the total of the weight of the components (a), (b) and (c) is 100 parts by weight.

The adhesive composition of the present invention may be blended with an inorganic or organic filler, organic composite filler, filler colorant or polymerization inhibitor such as hydroquinone as required in suitable amounts.

The adhesive composition of the present invention is used for dental or surgical purpose. Before the adhesive composition of the present invention is used for dental or surgical purpose, pretreatment is preferably made on a tooth or hard tissue (bone). The pretreatment includes, for example, etching of a surface to be bonded with an acid solution, modification of a surface to be bonded-with a primer, and etching and modification of a surface to be bonded with a primer having etching capability. The acid solution used for etching is exemplified by an aqueous solution comprising 5 to 60% by weight of phosphoric acid and an aqueous solution comprising 10% by weight of citric acid and 3% by weight of ferric chloride. The primer used for modification of a surface to be bonded is exemplified by an aqueous solution comprising 20 to 50% by weight of 2-hydroxyethyl (meth)acrylate and 1,3-dihydroxypropyl mono(meth)acrylate. As the primer having etching capability used for etching and modification of a surface to be bonded, an aqueous solution comprising an organic acid (including a monomer having an acidic group) and a component for modifying demineralized dentin and promoting the diffusion of an adhesive composition into dentin is preferably used. The component for promoting the diffusion of an adhesive composition into dentin is exemplified by monomers having a hydroxyl group such as alkylene glycol, polyalkylene glycol, 2-hydroxyethyl (meth)acrylate and 1,3-dihydroxypropyl mono(meth)acrylate; polyethylene glycol (meth)acrylate; and the like.

The polymerization initiator and the adhesive composition containing the same, provided by the present invention, have good affinity with living tissues, and are suitably used for adhesion restoration of the living tissues such as restoration of bonding of tooth, protection of injured portion of the soft tissue, fixing of bonding at the surgical treatment or the like.

[EXAMPLES]

The following examples and comparative examples further illustrate the present invention, but are in no way to be taken as limiting.

Abbreviations used herein represent the following compounds.

p-MMA/BuMA: a copolymer of methyl methacrylate and butyl methacrylate (molecular weight: 120,000, particle diameter: 68 μm, the content of MMA: about 25% by weight, manufactured by Fujikura Kasei Co. Ltd)

p-MMA/i-BuMA: a copolymer of methyl methacrylate and isobutyl methacrylate (molecular weight: 350,000, particle diameter: 0.7 μ, manufactured by Soken Kagaku Co. Ltd)

TBB.O: partially oxidized tributyl boron (manufactured by Sun Medical Co. Ltd, addition of oxygen: about 0.5 mole per mole of tributyl boron)

MMA: methyl methacrylate (manufactured by Wako Pure Chemical Industries Ltd, special-grade)

4-META: 4-methacryloxyethyl trimellitic anhydride (manufactured by Sun Medical Co. Ltd)

p-MMA: polymethyl methacrylate powder (number average molecular weight: 400,000, average particle diameter: about 25 μm, manufactured by Sun Medical Co. Ltd)

Examples 1 to 6 and Comparative Examples 1 to 4

(1) preparation of polymerization initiator composition:

Predetermined amounts of TBB.O and a solvent (and an oligomer or polymer which is inert to TBB.O) were charged into an Erlenmeyer flask equipped with a Teflon stirrer in a nitrogen box and stirred until a uniform solution or paste was obtained. The thus obtained polymerization initiator composition was charged into a 1-ml syringe having a needle inner diameter of 0.3 mm in a nitrogen atmosphere.

(2) performance of polymerization initiator composition:

Various tests were conducted on Examples 1 to 6 and Comparative Examples 1 to 4 having compositions shown in Table 1. The results are shown in Table 1.

The above tests were conducted in the following manners.

Ignition test: 0.5 ml or 10 drops (about 0.08 g) of the polymerization initiator composition is let fall on a filter paper or tissue paper to observe smoking, scorching or ignition of the filter paper or tissue paper visually.

Fluidity test: The polymerization initiator composition is dropped from the syringe to observe its fluidity visually.

good fluidity: The composition falls by each drop.

bad fluidity: The composition falls in a series of drops.

Activity test (measurement of curing time):

(1) 16 drops (0.32 g) of the polymerizable monomer consisting of MMA and 4-META in a weight ratio of 95/5 and 4 drops (0.02 to 0.03 g) of the polymerization initiator composition are taken to a dappen dish at 23°±2° C., and 0.36 g of p-MMA is added and mixed slightly for 10 seconds to prepare resin mud.

(2) Vaseline is thinly applied to a glass plate, a Teflon ring (outer diameter: 13 mm, inner diameter: 10 mm, thickness: 5 mm) thinly coated with vaseline is placed on the glass plate, and the resin mud is poured into the inside of the ring.

(3) Within 30 seconds after the start of mixing, the resin mud is transferred to an incubator maintained at a temperature of 37°±2° C. and a humidity of 100%, and a Vicat needle is placed on the surface of a test sample gently to check if a needle mark is left on the surface. The time elapsed from the start of mixing up to no trace of the needle mark on the test sample is taken as curing time.

TABLE 1

|  | Composition (weight ratio) | State | Fluidity |
| --- | --- | --- | --- |
| Example 1 | TBB.O/acetone = 54/30 | Colorless liquid | Good |
| Example 2 | TBB.O/tetrahydrofuran = 54/30 | Colorless liquid | Good |
| Example 3 | TBB.O/ethyl acetate = 54/30 | Colorless liquid | Good |
| Example 4 | TBB.O/hexane = 54/30 | Colorless liquid | Good |
| Example 5 | TBB.O/acetone/p-(MMA/BuMA) = 54/30/16 | Colorless paste (Observed through a microscope) | Good |
| Example 6 | TBB.O/acetone/p-(MMA/i-BuMA) = 54/30/16 | Colorless paste (Observed through a microscope) | Good |
| Comparative Example 1 | TBB.O | Colorless liquid | Good |
| Comparative Example 2 | TBB.O/p-(MMA/BuMA) = 54/16 | Colorless paste | Bad |
| Comparative Example 3 | TBB.O/p-(MMA/i-BuMA) = 54/16 | Colorless paste | Bad |
| Comparative Example 4 | TBB.O/vaseline = 54/16 | Colorless paste | Bad |

|  | Safety level against ignition* | | | | | | Curing time (seconds) |
| --- | --- | --- | --- | --- | --- | --- | --- |
|  | Test 1 | | | Test 2 | | | |
|  | Smoking | Scorching | Ignition | Smoking | Scorching | Ignition | |
| Example 1 | + | − | − | + | − | − | 300 |
| Example 2 | + | − | − | + | − | − | 330 |
| Example 3 | + | − | − | + | − | − | 330 |
| Example 4 | + | − | − | + | − | − | 360 |
| Example 5 | − | − | − | − | − | − | 300 |
| Example 6 | − | − | − | − | − | − | 300 |
| Comparative Example 1 | + | + | + | + | + | + | 290 |
| Comparative Example 2 | + | − | − | + | + | − | 330 |

TABLE 1-continued

| | | | | | | | |
|---|---|---|---|---|---|---|---|
| Comparative Example 3 | + | − | − | + | + | − | 330 |
| Comparative Example 4 | + | + | − | + | + | − | 360 |

*Test 1: dropped onto a filter paper (Whatman, No. 3)
Test 2: dropped onto a tissue paper,
+: smoking, scorching and ignition was observed
−: no smoking, scorching and ignition was observed

Example 7

(1) A surface to be bonded is prepared by exposing a dentin surface by cutting out the dentin surface of a foretooth of a bovine, while pouring water, and polishing with No. 600 emery paper.

After drying, the surface is treated with an etching solution containing 10% by weight of citric acid and 3% of ferric chloride for 10 seconds, washed with water for 10 seconds, and dried by air blow for 15 seconds. Thereafter, cellophane tape having a 4 mm diameter hole is adhered to the surface to define an area to be bonded.

(2) 4 drops (0.32 g) of a polymerizable monomer consisting of MMA and 4-META in a weight ratio of 95/5 and 1 drop (0.007 g) of the polymerization initiator composition of Example 5 are taken to a dappen dish, and 0.07 g of p-MMA and 0.07 g of $ZrO_2$ fine particles (average particle diameter: about 5 μm, surface coated with about 3% by weight of PMMA) are added, mixed slightly for 10 seconds to prepare resin mud.

(3) This resin mud is applied to the surface to be bonded prepared in (1), and an acryl bar is bonded to this surface to prepare a bonding test sample. This bonding test sample is left at room temperature for 30 minutes, immersed in distilled water at 37° C. for 24 hours and subjected to a tensile test to measure bonding strength between the acryl bar and the dentin. The bonding strength is an average value of five measurement values. The bonding strength was 12.8 MPa.

According to the present invention, an organic boron-based polymerization initiator composition having excellent safety against ignition, fluidity and polymerization activity is obtained and a dental or surgical adhesive having excellent safety, handling property, adhesive property and economic efficiency is also obtained.

What is claimed is:

1. A method of forming a polymerizable dental or surgical adhesive composition containing a polymerizable monomer and a polymerization initiator comprising an organic boron compound, which comprises mixing 30 to 90 parts by weight of (a) polymerizable monomer and 0 to 60 parts by weight of (b) (meth)acrylate polymer with from 1 to 30 parts by weight of (c) a polymerization initiation composition separately prepared from (i) 100 parts of organic boron compound as polymerization initiator, (ii) 10 to 150 parts by weight of aprotic solvent having a boiling point of from 30° to 150° C. and (iii) 5 to 100 parts by weight of a liquid or solid organic oligomer or polymer which is inert to the organic boron compound.

2. The method of claim 1 wherein polymerizable monomer (a) comprises (meth)acrylate or a combination of (meth)acrylate and a polymerizable monomer having an acidic group; the (meth)acrylate polymer (b) is selected from the group consisting of homo- or co-polymer of alkyl (meth)acrylate, copolymers of alkyl (meth)acrylate and other polymerizable monomers, copolymers of alkyl (meth)acrylate and alkylene di(meth)acrylate, and copolymers of alkyl (meth)acrylate and diene monomer; the organic boron compound (c)(i) is at least one compound selected from the group consisting of a trialkyl boron, alkoxyalkyl boron, dialkyl borane and partially oxidized trialkyl boron, the aprotic solvent (c)(ii) is a ketone, ether or ester, and the organic oligomer or polymer (c)(iii) is a homo- or co-oligomer or homo- or copolymer of alkyl (meth)acrylate.

3. The method of claim 1 wherein the organic boron compound is partially oxidized tributyl boron, the aprotic solvent is acetone, and the liquid or solid organic oligomer or polymer is a co-oligomer or copolymer of methyl methacrylate and (iso)butyl methacrylate.

4. A method of forming a polymerizable dental or surgical adhesive composition containing a polymerizable monomer and a polymerization initiator comprising an organic boron compound, which comprises mixing 30 to 90 parts by weight of (a) polymerizable monomer and 0 to 60 parts by weight of (b) (meth)acrylate polymer with from 1 to 30 parts by weight of (c) a polymerization initiation composition separately prepared from (i) 100 parts by weight of organic boron compound as polymerization initiator and (ii) 10 to 150 parts by weight of aprotic solvent having a boiling point of from 30° to 150° C.

5. A polymerizable dental or surgical adhesive composition containing a polymerizable monomer and a polymerization initiator comprising an organic boron compound, which is prepared by the method of claim 4.

6. A polymerizable dental or surgical adhesive composition containing a polymerizable monomer and a polymerization initiator comprising an organic boron compound, which is prepared by the method of claim 3.

* * * * *